(12) United States Patent
Engel et al.

(10) Patent No.: US 8,389,497 B2
(45) Date of Patent: *Mar. 5, 2013

(54) USE OF ALKYLPHOSPHOCHOLINES IN COMBINATION WITH ANTITUMOR MEDICATIONS FOR THE TREATMENT OF BENIGN AND MALIGNANT ONCOSES IN HUMANS AND MAMMALS

(75) Inventors: Jürgen Engel, Alzenau (DE); Eckhard Günther, Maintal (DE); Herbert Sindermann, Rodgau (DE)

(73) Assignee: AEterna Zentaris GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/632,187

(22) Filed: Jul. 30, 2003

(65) Prior Publication Data

US 2004/0097470 A1 May 20, 2004

Related U.S. Application Data

(60) Provisional application No. 60/399,615, filed on Jul. 30, 2002.

(51) Int. Cl.
*A61K 31/70* (2006.01)
*A61K 31/685* (2006.01)

(52) U.S. Cl. .......................... 514/49; 514/77
(58) Field of Classification Search .............. 514/78, 514/89, 49, 77
See application file for complete search history.

(56) References Cited

U.S. PATENT DOCUMENTS

| | | | | |
|---|---|---|---|---|
| 5,219,866 | A * | 6/1993 | Schumacher et al. | 514/315 |
| 5,942,639 | A * | 8/1999 | Engel et al. | 558/146 |
| 6,093,704 | A * | 7/2000 | Nickel et al. | 514/77 |
| 6,172,050 | B1 * | 1/2001 | Nossner et al. | 514/79 |
| 6,583,127 | B1 | 6/2003 | Gajate et al. | |
| 6,696,428 | B2 * | 2/2004 | Nickel et al. | 514/77 |
| 6,903,080 | B2 | 6/2005 | Nossner et al. | |
| 2007/0167408 | A1 | 7/2007 | Perrissoud et al. | |
| 2011/0243933 | A1 | 10/2011 | Poradosu et al. | |

FOREIGN PATENT DOCUMENTS

| EP | 1 545 553 B1 | 7/2011 |
|---|---|---|
| WO | WO 00/33917 | 6/2000 |
| WO | WO 02/066019 A2 | 8/2002 |
| WO | WO 03/005522 A1 | 7/2003 |
| WO | WO 2005/000318 | 1/2005 |
| WO | WO 2006/081452 | 8/2006 |
| WO | WO 2011/123691 A1 | 10/2011 |

OTHER PUBLICATIONS

Goodman &Gilman's, The Pharmacological Basis of Therapeutics, Ninth Edition, (1996), Calabresi et al., Section X, Chemotherapy of Neoplastic Diseases, pp. 1225-1232.*
Hilgard et al. cancer Chemother. Pharmcol. (1993) 32: 90-95.*
Patel et al., Cancer research, 62, 1401-1409, Mar. 1, 2002.*
Kasianenko et al, topical use of Miltex in patients with Breast Cancer's cutaneous manifestations, 1998:87. (2pages) Abstract only.*
Manfred E. Wolff, Burger's Medicinal Chemistry and Drug Discovery, 5th edition, vol. 1, 1995, pp. 975-977.*
Gilbert S. Banker, Modern Pharmaceutic.s, 3rd edition, 1996, p. 596.*
Georgieva et al. Cancer Letters 182(2) 163-174 (2002).*
Aicher et al. Abstract #203—22nd EORTC-NCI-AACR Symposium on Molecular Targets and Cancer Therapeutics (Nov. 17, 2010).*
Thilo Sprub, Gunther Bernhardt, Helmut Schoenenberger and Jurgen Engel, Antitumor activity of miltefosine alone and after combination with platinum complexes on MXT mouse mammary carcinoma models; J Cancer Res Clin Oncol (1993) 119:142-149 (XP-000905599).
P. Hilgard, J. Stekar, T. Klenner, G. Nossner, B. Kutscher, and J. Engel; Heterocyclic Alkylphospholipids With an Improved Therapeutic Range; Advances in Experimental Medicine and Biology, United States (1996), 157-164 (XP-002256712).
J. Stekar, P. Hilgard and T. Klenner; Opposite Effect of Miltefosine on the Antineoplastic Activity and Haematological Toxicity of Cyclophosphamide; Eur F Cancer, vol. 31A, No. 3, pp. 372-374, 1995 (XP-002256713).
Milka C. Georgieva, Spiro M. Konstantinov, Margarit Topashka-Ancheva, Martin R. Berger; Combination effects of alkylphosphocholines and gerncitabine in malignant and normal hematopoietic cells; Cancer Letters 182 (2002) 163-174 (XP-002256714).
D Berkovic, Eam Fleer, J Breass, J Pfortner, E Schleyer and W Hiddenmann; The influence of 1-B-D-arabinofuranosylcytosine on the metabolism of phosphatidylcholine in human leukemic HL 60 and Raji cells; Leukemia (1997) 11, 2079-2086 (XP-002256715).
Shoji M.; Raynor R.L.; Fleer E.A.; Eibl H.; Vogler W.R.; Kuo J.F.; Effects of hexadecylphosphocholine on protein kinase C and TPA-induced differentiation of HL60 cells; Journal Article (Feb. 1991) vol. 26, No. 2, 145-149 (XP-002256716).
International Search Report.
Principe et al., Synergistic cytotoxic effect of aza-alkylphospholipids in association with chemotherapeutic drugs, J. Lipid Mediators Cell Signalling, 10, 1994, pp. 171-173.
Principe et al., Evaluation of combinations of antineoplastic ether phospholipids and chemotherapeutic drugs, Anti-Cancer Drugs, 3, 1992, pp. 577-587.
Ruiter et al., Alkyl-Lysophospholipids As Anticancer Agents and Enhancers of Radiation-Induced Apoptosis, Int. J. Radiation Oncology Biol. Phys., 49(2), 2001, pp. 415-419.
Maly et al., Interference of new alkylphospholipid analogues with mitogenic signal transduction, Anti-Cancer Drug Design. 10. 1995. pp. 411-425.

(Continued)

*Primary Examiner* — Shirley V Gembeh
(74) *Attorney, Agent, or Firm* — Goodwin Procter LLP

(57) ABSTRACT

The invention relates to the use of alkylphosphocholines in combination with antitumor medicaments for the treatment of benign and malignant oncoses in humans and animals. It is possible in this connection for the alkylphosphocholines to be employed in a combination according to the invention with one or a combination of various approved cytostatics. Preferred alkylphosphocholines are described by the Formula II.

Formula II

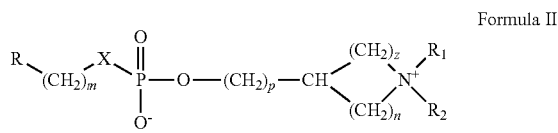

5 Claims, No Drawings

OTHER PUBLICATIONS

Lohmeyer et al., Antitumor ether lipids and alkylphosphocholines, Drugs of the Future, 19(11), 1994, pp. 1021-1037.

Hilgard et al, D-21266, a New Heterocyclic Alkylphospholipid with Antitumour Activity, European Journal of Cancer, 33(3), 1997, pp. 442-446.

Australian Search Report.

Chou, Ting-Chao, Drug Combination Studies and Their Synergy Quantification Using the Chou-Talalay Method, Molecular Pharmacology and Chemistry Program, Memorial Sloan-Kettering Cancer Center, New York, NY USA. Cancer Reseach (2010), 70(2), 440-446.

Chou, Ting-Chao et al., Quantitative analysis of dose-effect relationships: the combined effects of multiple drugs or enyzme inhibitors, Lab. Pharmacol., Mem. Sloan-Kettering Cancer Cent., New York, NY, USA. Advances in Enzyme Regulation (1984), 22 27-55.

Pagé Brigitte, et al., A new fluorometric assay for cytotoxicity measurements in vitro, International Journal of ONcology 3: 473-476, 1993.

European Search Report dated Sep. 3, 2008.

ASCO Abstract 2006—Journal of Clinical Oncology, 2006 ASCO Annual Meeting Proceedings (Post-Meeting Edition)m vol. 24, No. 18S (Jun. 20 Supplement), 2006.

ASCO Abstract 2009—Journal of Clinical Oncology, 2009 ASCO Annual Meeting Proceedings (Post-Meeting Edition)m vol. 27, No. 15S (May 20 Supplement), 2009:4081.

Ayala, Gustavo, et al., Bortezomib-Mediated Inhibition of Steroid Receptor Coactivator-3 Degradation Leads to Activated Akt, Clin Cancer Res, Nov. 15, 2008, 7511-7518, 14(22).

Catley Laurence, et al., Alkyl Phospholipid Perifosine Induces Myeloid Hyperplasia in a Murine Myeloma Model, Experimental Hematology, 35 (2007), 1038-1046.

Chiarini, F., et al., The novel Akt Inhibitor, Perifosine, Induces Caspase-Dependent Apoptosis and Downregulates P-glycoprotein Expression in Multidrug-Resistant Human T-acute Leukemia Cells by a JNK-dependent Mechanism, Leukemia (2008) 22, 1106-1116.

Cirstea, Diana, et al., Dual Inhibition of Akt/Mammalian Target of Rapamycin Pathway by Nanoparticle Albumin-Bound-Rapamycin and Perifosine Induces Antitumor Activity in Multiple Myeloma, Mol Cancer Ther, Apr. 2010, 963-975, 9(4).

Crul, M., et al. Phase I and Pharmacological Study of Daily Oral Administration of Perifosine (D-21266) in Patients with Advanced Solid Tumours, European Journal of Cancer, 38 (2002), 1615-1621.

Dasmahapatra Girija P., et al., In vitro Combination Treatment with Perfosine and UCN-01 Demonstrates Synergism Against Prostate (PC-3) and Lung (A549) Epthithelial Adenocarcinoma Cell Lines, Clin Cancer Res, Aug. 1, 2004, 5242-5252, vol. 10.

David, E., et al., Perifosine Synergistically Enhances TRAIL-Induced Myeloma Cell Apoptosis via Up-Regulation of Death Receptors, Clin Cancer Res 2008:14(16) Aug. 15, 2008, 5090-5098.

Dogan, S. Serdar, Ocular Side Effects Associated with Imatinib Mesylate and Perifosine for Gastrointestinal Stromal Tumor, Hematol Oncol. Clin N Am, 23 (2009) 109-114.

Ellis, Matthew J., et al., "PIKing" the Winner for Phosphatidylinositol 3-Kinase Inhibitors in ErbB2-Positive Breast Cancer: Let's Not "PTENed" It's Easy!, Clin Cancer Res, Oct. 1, 2007, 5661-5662, 13(19).

Engel, Jörg B., et al., Induction of Programmed Cell Death by Inhibition of AKT with the Alkylphosphochloine Perifosine in In Vitro Models of Platinum Sensitive and Resistant Ovarian Cancers, Arch Gynecol Obstet, doi:10.1007/s00404-010-1457-6; published online Apr. 20, 2010.

Engel, Jörg B., et al., Perifone Inhibits Growth of Human Experimental Endometrial Cancers by Blockade of AKT Phosphorylation, Eur J. Obstet. Gynecol (2008), doi:10.1016/j.ejogrb.2008.06.007.

Ernst, D. Scott, et al. Phase II Study of Perifosine in Previously Untreated Patients with Metastatic Melanoma, Investiational New Drugs, 23:569-576, 2005.

Festuccia, Claudio, et al., Akt Down-Modulation Induces Apoptosis of Human Prostate Cancer Cells and Synergizes with EGFR Tyrosine Kinase Inhibitors, The Prostate, 58:965-974 (2008).

Floryk, Daniel, et al., Perifosine Induces Differentiation and Cell Death in Prostate Cancer Cells, Cancer Letters, 266 (2008) 216-226.

Fomchenko, Elena I., et al., Mouse Models of Brain Tumors and Their Applications in Preclinical Trials, Clin Cancer Res., 2006:12(18) Sep. 15, 2006; 5288-5297.

Fu, Lei, et al., Perifosine Inhibits Mammalian Target of Rapamycin Signaling through Facilitating Degradation of Major Components in the mTOR Axis and Induces Autophagy, Cancer Res, Dec. 1, 2009, 8967-8976, 69(23).

Gajate, Consuelo, et al., Edelfosine and Perifosine Induce Selective Apoptosis in Multiple Myeloma by Recruitment of Death Receptors and Downstream Signaling Molecules into Lipids Rafts, Blood, Jan. 15, 2007, 711-719, vol. 109, No. 2.

Gills, Joell, et al., Perifosine: Update on a Novel Akt Inhibitor, Current Oncology Reports-Evolving Therapies, 11:102-110.

Harvey, R. Donald, et al., P13 Kinase/AKT Pathway as a Therapeutic Target in Multiple Myeloma, Future Oncol., (2007) 3(6), 639-647.

Hideshima, Teru, et al., Perifosine, An Oral Bioactive Novel Alkylphospholipid, Inhibits Akt and Induces In Vitro and In Vivo Cytotoxicity in Human Multiple Myeloma Cells, Blood First Edition Paper, Jan. 17, 2006, 1-34, doi 10.1182/blood-2005-08-3434.

Hideshima, Teru, et al., Inhibition of Akt Induces Significant Downregulation of Survivin and Cytotoxicity in Human Multiple Myeloma Cells, British Journal of Haematology, 2007, 138, 783-791.

Huston, Alissa, et al., Targeting and Heat Shock Protein 90 Produces Synergistic Multiple Myeloma Cell Cytotoxicity in the Bone Marrow Microenvironment, Clin Cancer Res, Feb. 1, 2008, 865-874, 14(3).

Jendrossek, V., et al., Membrane Targeted Anticancer Drugs: Potent Inducers of Apoptosis and Putative Radiosensitisers, Curr. Med. Chem.—Anti-Cancer Agents, 2003, 3, 343-353.

Knowling, M., et al., A Phase II Study of Perifosine (D-21226) in Patients with Previously Untreated Metastatic or Locally Advanced Soft Tissue Sacoma: A National Cancer Institue of Canada Clinical Trials Group Trial, Invest New Drugs, (2006), 24:435-439.

Kodach, Liudmila L., vilacein Synergistically Increases 5-fluorouracil Cytotoxicity, Induces Apoptosis and Inhibits Akt-mediated Signal Transduciton in Human Colorectal Cancer Cells, Carcinogenesis, 2006, vol. 27, No. 3, 508-516.

Konstantinov, Spiro M., et al., BCR-ABL Influences the Antileukaemic Efficacy of Alkylphosphocholines, British Journal of Haematology, 1999, 107, 365-374.

Konstantinov, Spiro M., et al., Human Urinary Bladder Carcinoma Cell Lines Respond to Treatment with Alkylphosphocholines, Cancer Letters, 1999, 144, 153-160.

Konstantinov, Spiro M., et al., Alkylphosphocholines: Effects on Human Leukemic Cell Lines and Normal Bone Marrow Cells, Int. J. Cancer, 1998, 77, 778-786.

Kumar, Anil, et al., The Alkylphospholipid Perifosine Induces Apoptosis and p21-Mediated Cell Cycle Arrest in Medulloblastoma, Mol Cancer Res, Nov. 2009, 1813-1821, 7(11).

Leighl, Natasha B., et al., A Phase 2 Study of Perifosine in Advanced or Metastatic Breast Cancer, Breast Cancer Res Treat (2008), 108:87-92.

Leleu, Xavier, et al., Targeting NF-κB in Waldenstrom Macroglobulinemia, Blood, May 15, 2008, 111(10), 5068-5077.

Li, X., et al., Enhancement of Antitumor Activity of the Anti-EGF Receptor Monoclonal Antibody Cetuximab/C225 by Perifosine in PTEN-deficient Cancer Cells, Onocogen, (2005), 1-11.

Lopiccolo, Jaclyn, et al., Targeting the P13K/Akt/mTOR Pathway: Effective Combinations and Clinical Considerations, Drug Resistance Updates, 11 (2008) 32-50.

Mitsiades, Constantin S., et al., Emerging Treatments for Multiple Myeloma: Beyond Immunomodulatory Drugs and Bortezomib, Seminars in Hematology, Apr. 2009, vol. 46, No. 2, 166-175.

Momota, Hiroyuki, et al., Perifosine Inhibits Multiple Signaling Pathways in Glial Progenitors and Cooperates With Temozolomide to Arrest Cell Proliferation in Gliomas In Vivo, Cancer Res, Aug. 15, 2005, 65(16), 7429-7435.

Nelson, EC, et al., Inhibition of Akt Pathways in the Treatment of Prostate Cancer, Prostate Cancer and Prostatic Diseases, (2007), 10, 331-339.

NyÅkern, Maria, et al., Synergistic Induction of Apoptosis in Human Leukemia T Cells by the Akt Inhibitor Perifosine and Etoposide Through Activation of Intrinsic and Fas-mediated Extrinsic Cell Death Pathways, Mol Cancer Ther, Jun. 2006, 5(6), 1559-1570.

Papa, V., et al., Proapoptotic Activity and Chemosensitizing Effect of the Novel Akt Inhibitor Perifosine in Acute Myelogenous Leukemia Cells, Leukemia, (2008), 22, 147-160.

Patel, Vyomesh, Perifosine, A Novel Alkylphospholipid, Induces p21WAF1 Expression in Squamous Carcinoma Cells Through a P53-independent Pathway, Leading to Loss in Cyclin-dependent Kinase Activity and Cell Cycle Arrest, Cancer Research, 62, 1401-1409, 2002.

Porta, Camillo, et al., Phosphatidylinositol-3-Kinase/Akt Signaling Pathway and Kidney Cancer, and the therapeutic Potential of Phosphatidylinositol-3-Kinase/Akt Inhibitors, The Journal of Urology, Dec. 2009, vol. 182, 2569-2577.

Rahmani, Mohamed, et al., Coadmininstration of Histone Deacetylase Inhibitors and Perifosine Synergistically Induces Apoptosis in Human Leukemia Cells Through Akt and ERK1/2 Inactivation and the Generation of Ceramide and Reactive Oxygen Species, Cancer Res, 2005, 2422-2432.

Tazaari, Pier Luigi, et al., Synergistic Proapoptotic Activity of Recombinant TRAIL Plus the Akt Inhibitor Perifosone in Acute Myelogenous Leukemia Cells, Cancer Res, Nov. 15, 2008, 68 (22), 9394-9403.

Ummersen et al., A Phase I Trial of Perifosine (NSC 639966) on a Loading Dose/Maintenance Dose Schedule in Patients with Advanced Cancer, Clinical Cancer Research, vol. 10, 7450-7456, Nov. 15, 2004.

Unger, Clemens, et al., First-Time-In-Man and Pharmacokinetic Study of Weekly Oral Perifosine in Patients with Solid Tumours, European Journal of Cancer, 46 (2010), 920-925.

Vinall, Ruth L., et al., Combination Treatment of Prostate Cancer Cell Lines with Bioactive Soy Isoflavones and Perifones Causes Increased Growth Arrest and/or Apoptosis, Clin Cancer Res, Oct. 15, 2007, 13(20), 6204-6216.

Vink, Stefan R., et al., Tumor and Normal Tissue Pharmacokinetics of Perifosine, An Oral Anti-Cancer Alkylphospholipid, Investigational New Drugs, 23, 2005, 279-286.

Vink, Stefan R., et al., Phase I and Pharmacokinetic Study of Combined Treatment With Perifosine and Radiation in Patients With Advanced Solid Tumours, Radiotherapy and Oncology, 80, 2006, 207-213.

Voltan, R., et al., Perifosine Plus Nutlin-3 Combination Shows a Synergistic Anti-Leukaemic Activity, British Journal of Haematology, 2010, 148(6), 957-961.

Younes, Hashem, et al., Targeting the Phosphatidylinositol 3-Kinase Pathway in Multiple Myeloma, Clin Cancer Res, Jul. 1, 2007, 13(13), 3771-3775.

Aicher, B. et. al., Perifosine in Combination with Antimetabolites Induces Synergistic Effects on Cytotoxicity and Apoptosis in Human Colon, Multiple Myeloma, Breast, Renal, and Liver Tumor Cell Lines, Abstract #203—22nd EORTC-NCI-AACR Symposium on Molecular Targets and Cancer Therapeutics, Nov. 17, 2010.

O. Miyazaki, M. Hiratsuka and H. Sugihara, Activation of Caspase 3-Like Protease Is Essential to Octadecyl-(1,1-Dimethyl-4-Piperidino-4-YL)-Phosphate (D-21266)-Induced Apoptosis in Human Squamous Cell Carcinoma KB Cells, Drugs of Today 1998, 34 (Suppl. F): 51-57.

Oliver Rosen, Christiane Schymanietz and Fritz Hölzel, Antiproliferative, cytotoxic and recovery effects in tumor cell cultures treated with synthetic pholpholipids, International Journal of Oncology 5: 517-523, 1994.

Gottfried Konecny, Michael Untch, Neddis Slamon, Malgorzatta Beryt, Steffen Kahlert, Margret Felber, Elena Langer, Sandra Lude, Hermann Hepp, and Mark Pegram, Drug interactions and cytotoxic effects of paclitaxel in combination with carboplatin, epirubicin, gemcitabine or vinorelbine in breast cancel cell lines and tumor samples, Mark E. Lippman, MD., Editor-in-Chief, Breast Cancer Research and Treatment 67: 223-233, 2001, Kluwer Academic Publishers, *Printed in the Netherlands*, Report.

C. Kent Osborn, Libbey Kitten, and Carlos L. Arteaga, Antagonism of Chemotherapy-Induced Cytotoxicity for Human Breast Cancer Cells by Antiestrogens, Clinical Oncology—Official Journal of the American Society of Clinical Oncology, Grune & Stratton, Harcourt Brace Jovanovich, Inc., vol. 7, No. 6, Jun. 1989.

R. Lopez Lopez, R.E.N. van Rijswijk, J. Wagstaff, H.M. Pinedo and G.J. Peters, The Synergistic and Antagonistic Effects of Cytotoxic and Biological Agents on the In Vitro Antitumour Effects of Suramin, The European Journal of Cancer (EJC), vol. 30A No. 10, 1545-1549, Published in Oct. 1994.

Daniel R. Budman and Anthony Calabro, In vitro search for synergy and antagonism: evaluation of docetaxel combinations in breast cancer cell lines, Marc E. Lippmann, MD., Editor-In-Chief, Breast Cancer Research and Treatment, vol. 74: 41-46, No. 1, July (I) 2002, Kluwer Academic Publishers, *Printed in the Netherlands*.

O. Safa, S.M. Parkin and M.C. Bibby, Morphological Changes and Cytokine Gene Expression in Tumor Xenografts Following Treatment With the Alkylphosphocholines Hexadecylphosphocholine and Perifosine, Drugs of Today 1998, 34 (Suppl. F.): 15-26.

Sudhir B. Kondapaka, Sheo S. Singh, Girija P. Dasmahapartra, Edward A. Sausville, and Krishnendu K. Roy, Perifosine, a novel alkylphospholipid, inhibits protein kinase B activation, Molecular Cancer Therapeutics 2003; 2:1093-1103.

* cited by examiner

USE OF ALKYLPHOSPHOCHOLINES IN COMBINATION WITH ANTITUMOR MEDICATIONS FOR THE TREATMENT OF BENIGN AND MALIGNANT ONCOSES IN HUMANS AND MAMMALS

CROSS-REFERENCE TO RELATED APPLICATIONS

This application claims the benefit of U.S. Provisional Application No. 60/399,615, filed Jul. 30, 2002, which is hereby incorporated by reference.

BACKGROUND OF THE INVENTION

Alkylphosphocholines are a new class of organic compounds, which exhibit diversified anti-neoplastic activities (M. Lohmeyer and R. Bittman, Antitumor Ether Lipids and Alkylphosphocholines, DOF, 19 (11), 1021-103 7 (1994)). The effect of the alkylphosphocholines in this connection may be based on different, molecular and biochemical mechanisms, some of which take place on the level of the plasma membrane of the cell.

It is well known that alkylphosphocholines influence inositol metabolism, the interaction with phospholipases or inhibition of protein kinase C and thus that this class of substances has a general influence on cellular signal transduction (K. Maly et al., Interference of New Alkylphospholipid Analogues With Mitogenic Signal Transduction, Anti-Cancer Drug Design, 10, 411-425 (1995); and P. Hilgard, et al., D21266, A New Heterocyclic Alkylphospholipid with Anti-tumor Activity, Eur. J. Cancer, 33 (3), 442-446 (1997)). Thus, the alkylphosphocholine perifosine shows growth-inhibitory properties in relation to various melanoma melanoma, CNS, lung, colon, prostate and breast cancer cell lines with an $IC_{50}$ ranging from 0.2 to 20 μM.

It is further known that perifosine blocks tumor cells in the $G_1$-S and $G_2$-M phase of the cell cycle (V. Patel, et al., A Novel Alkylphospholipid, Induces p.21 $^{Waf1}$ Expression in Squamous Carcinoma Cells through a p53-independent Pathway, Leading to Loss in Cyclindependent Kinase Activity and Cell Cycle Arrest, Cancer Research 62, 1401-1409 (2002)).

It is known that the use of alkylphosphocholines before or together with radiation therapy leads its synergistic effects during the treatment of tumors (P. Principe et al., Evaluation of Combinations of Antineoplastic Ether Phospholipids and Chemotherapeutic Drugs, Anti-Cancer Drugs, 3 (6), 577-587 (1992)). It has also been reported that different glycerol-3-phospholipids, such as ET-18-OOCH$_3$, in combination with different DNA-interacting substances or tubulin binders increase the anti-tumor activity in vitro in a different tumor cell lines (P. Principe et al., Synergistic Cytotoxic Effect of Aza-alkylphospholipids in Association with Chemotherapeutic Drugs, J. Lipid Mediators Cell Signalling, 10 (1-2), 171-173 (1994)).

BRIEF SUMMARY OF THE INVENTION

Surprisingly, it was now possible to show that linear alkylphosphocholines of the general Formulas I and II are suitable for use in a combination according to the invention with other drug products for the treatment of benign and malignant oncoses in humans and mammals.

In this connection, the present invention relates to the novel use of alkylphosphocholine in combination with antitumor medications for art-recognized therapeutic activities attributed to the treatment of benign and malignant oncoses in humans and mammals.

It is therefore an object of this invention to provide a novel means of treating tumors with an inventive combination of linear alkylphosphocholines and anti-tumor substances.

DETAILED DESCRIPTION OF THE INVENTION

The present invention provides a novel use of linear alkylphosphocholines of the general Formulas I and II in an inventive combination with other medicinal drugs for the treatment of benign and malignant oncoses in humans and mammals. According to one aspect of the invention, the compounds of the general Formulas I and II can be used in an inventive combination with anti-tumor substances. Anti-tumor substances may be alkylating agents, anti-metabolites, plant alkaloids, platinum compounds, tumor antibiotics and agonists or antagonists of natural hormones. The anti-tumor substances may be selected from, but are not restricted to cis-platinum, carboplatinum, oxaliplatinum, bleomycin, doxorubicin, methotrexate, paclitaxel, docetaxel, vincristine, vinblastine, etoposide, teniposide, ifosfamide, cyclophosphamide, 5-fluorouracil, fludarabin, gemcitabin and cytarabin.

It is moreover possible for the alkylphosphocholines of the general Formula I and II to be employed in a claimed combination with inhibitors of signal transduction in the form of high and low molecular weight inhibitors of receptor and/or cytosolic kinases. These inhibitors may be selected from but not restricted to monoclonal antibodies and heterocyclic compounds.

The alkylphosphocholines of the general Formulas I and II, on which the invention is based, may be used in the form of finished medicinal drugs.

The compounds, on which the invention is based, are described by the general Formulas I and II:

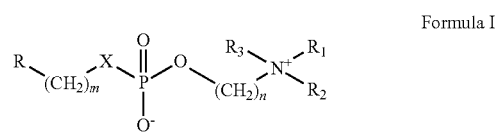

Formula I

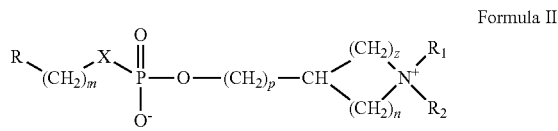

Formula II in which, independently of one another,
n, m, p, z is a whole number between 0 and 4,
X is O, S, NH;
R is hydrogen, a linear or branched $C_1$ to $C_{20}$ alkyl group, which may be saturated or unsaturated with one to three double and/or triple bonds and unsubstituted or optionally substituted at the same or at different carbon atoms with one, two or more halogen, nitro, cyano, hydroxy, $C_1$ to $C_6$ alkoxy, amino, mono-($C_1$ to $C_4$) alkylamino or di($C_1$ to $C_4$) alkylamino groups,
$R_1$, $R_2$, $R_3$ independently of one another represent hydrogen, a linear or branched ($C_1$ to $C_6$) alkyl group, preferably methyl and ethyl, a ($C_3$ to CO cyclo alkyl group, which may be unsubstituted or optionally substituted at the same or different carbon atoms with one, two or more halogen, nitro, cyano, hydroxy, $C_1$ to $C_6$ alkoxy, amino, mono-($C_1$ to $C_4$) alkylamino or di-($C_1$ to $C_4$) alkylamino groups.

According to a further aspect of the invention, a method for controlling tumors in humans and in mammals is provided and comprises administering at least one of the compounds of the general Formula I and II on which the invention is based to the human or a mammal in an amount effective for tumor treatment before or during a treatment with approved antitumor substances.

The therapeutically effective dose, to be administered for the treatment, of the particular compound of the general formula I and II on which the invention is based depends inter alia on the nature and the stage of the oncosis, the age and sex of the patient, the mode of administration and the duration of treatment.

The compounds on which the invention are based can be administered in a drug product as liquid, semisolid and solid drug forms. This takes place in the manner suitable in each case in the form of aerosols, oral powders, dusting powders and epipastics, uncoated tablets, coated tablets, emulsions, foams, solutions, suspensions, gels, ointments, pastes, pills, pastilles, capsules or suppositories.

EXAMPLES

Example 1

Administration of Perifosine (D-21 266) in Combination with cisplatin

| In vivo Experiment: | DMBA-induced rat mammary carcinoma model |
| --- | --- |
| Experimental Animal: | Sprague-Dawley rat, female |
| Procedure: | The mammary carcinoma was induced by a single oral dose of DMBA. The animals received perifosine from day 0 to day 14 and were observed up to day 42. The weight of the tumor mass was estimated by palpation and comparison with plastic models. The initial weight is set equal to 100%. |
| Administration: | Perifosin 14 × 6.81 mg/kg p.o. |
| | Cis-platinum 4 × 1 mg/kg i.p. |
| Effect: | Reduction in the tumor was distinctly greater and longer through the combination treatment than through the single treatment in each case. |

TABLE 1

| Treatment | Tumor Starting Weight (g) | Day 21, Change in % | p Test vs. Control |
| --- | --- | --- | --- |
| Control | 1.0 | 875 | — |
| Perifosin (D-21266) | 0.9 | −25 | <0.001 |
| Cis-platinum | 0.9 | 410 | 0.120 |
| Perifosin (D-21266) + Cis-platinum | 0.8 | −75 | <0.001 |

Example 2

Administration of Perifosine in Combination with Cyclophosphamide

| In vivo Experiment: | DMBA-induced rat mammary carcinoma model |
| --- | --- |
| Experimental Animal: | Sprague-Dawley rat, female |
| Procedure: | The mammary carcinoma was induced by a single oral dose of DMBA. The animals received perifosine from day 0 to day 14 and were observed up to day 42. The weight of the tumor mass was estimated by palpation and comparison with plastic models. The initial weight is set equal to 100%. |
| Administration: | Perifosine 14 × 6.81 mg/kg p.o. |
| | Cyclophosphamide 100 mg/kg, VZ 0, i.v. |
| Effect: | Reduction in the tumor was distinctly greater and longer through the combination treatment than through the single treatment in each case. |

TABLE 2

| Treatment | Tumor Starting Weight (g) | Day 21, Change in % | p Test vs. Control |
| --- | --- | --- | --- |
| Control | 1.0 | 875 | — |
| Perifosin (D-21266) | 0.9 | −25 | <0.001 |
| Cyclophosphamide | 0.9 | 500 | 0.011 |
| Perifosin (D-21266) + Cyclophosphamide | 0.8 | −83.3 | <0.001 |

Example 3

Administration of Perifosine in Combination with Adriamycin

| In vivo Experiment: | DMBA-induced rat mammary carcinoma model |
| --- | --- |
| Experimental Animal: | Sprague-Dawley rat, female |
| Procedure: | The mammary carcinoma was induced by a single oral dose of DMBA. The animals received perifosine from day 0 to day 14 and were observed up to day 42. The eight of the tumor was mass was estimated by palpation and comparison with plastic models. The initial weight is set equal to 100%. |
| Administration: | Perifosine 14 × 6.81 mg/kg p.o. |
| | Adriamycin 4 × 2.15 mg/kg i.p. |
| Effect: | Reduction in the tumor was distinctly greater and longer through the combination treatment than through the single treatment in each case. |

TABLE 3

| Treatment | Tumor Starting Weight (g) | Day 21, Change in % | p Test vs. Control |
| --- | --- | --- | --- |
| Control | 1.0 | 875 | — |
| Perifosin (D-21266) | 0.9 | −25 | <0.001 |
| Adriamycin | 1.0 | 781 | 0.197 |
| Perifosin (D-21266) + Adriamycin | 1.9 | −70 | <0.001 |

In the manner described above, the present invention thus provides a method for the use of alkylphosphochlorines in combination with antitumor medications for the treatment of benign and malignant oncoses in humans and mammals. While this invention has been described with reference to the preferred embodiments, these are illustrative only and not limiting, having been presented by way of example. Other modifications will become apparent to those skilled in the art by study of the specification and drawings. It is thus intended that the following appended claims include such modifications as fall within the spirit and scope of the present invention.

The invention claimed is:

1. A method of treating mammary carcinoma, wherein said method comprises administering a therapeutically effective amount of octadecyl 1,1-dimethylpiperidinium-4-yl phosphate (perifosine) before and/or during treatment with an antimetabolite antitumor substance selected from the group consisting of 5-fluorouracil, fludarabine, cytarabine, and methotrexate.

2. The method of claim 1 wherein said antimetabolite antitumor substance is 5-fluorouracil.

3. The method of claim 1 wherein said antimetabolite antitumor substance is fludarabine.

4. The method of claim 1 wherein said antimetabolite antitumor substance is cytarabine.

5. The method of claim 1 wherein said antimetabolite antitumor substance is methotrexate.

* * * * *